(12) United States Patent
Wan et al.

(10) Patent No.: US 10,469,718 B2
(45) Date of Patent: Nov. 5, 2019

(54) CAMERA MODULE HAVING BAFFLE BETWEEN TWO GLASS SUBSTRATES

(71) Applicant: OmniVision Technologies, Inc., Santa Clara, CA (US)

(72) Inventors: Tsung-Wei Wan, Hsinchu County (TW); Wei-Ping Chen, New Taipei (TW)

(73) Assignee: OmniVision Technologies, Inc., Santa Clara, CA (US)

( * ) Notice: Subject to any disclaimer, the term of this patent is extended or adjusted under 35 U.S.C. 154(b) by 0 days.

(21) Appl. No.: 15/585,483

(22) Filed: May 3, 2017

(65) Prior Publication Data

US 2018/0324336 A1 Nov. 8, 2018

(51) Int. Cl.
| H04N 5/225 | (2006.01) |
| G03B 17/08 | (2006.01) |
| G02B 23/24 | (2006.01) |
| G02B 13/00 | (2006.01) |
| A61B 1/00 | (2006.01) |

(52) U.S. Cl.
CPC ....... *H04N 5/2254* (2013.01); *A61B 1/00186* (2013.01); *G02B 13/0085* (2013.01); *G02B 23/2407* (2013.01); *G02B 23/2484* (2013.01); *G03B 17/08* (2013.01); *H04N 5/2257* (2013.01); *H04N 2005/2255* (2013.01)

(58) Field of Classification Search
CPC .. H04N 5/2254; H04N 5/2252; H04N 5/2257; G02B 5/208
See application file for complete search history.

(56) References Cited

U.S. PATENT DOCUMENTS

| 9,349,765 | B2 * | 5/2016 | Wan | G02B 7/02 |
| 2005/0179805 | A1 * | 8/2005 | Avron | G02B 7/022 348/340 |
| 2006/0171704 | A1 * | 8/2006 | Bingle | B60R 11/04 396/419 |
| 2007/0126912 | A1 * | 6/2007 | De Bruin | H01L 31/0203 348/340 |
| 2010/0079642 | A1 | 4/2010 | Kurimoto et al. | |
| 2010/0176281 | A1 * | 7/2010 | Tomioka | G02B 7/022 250/227.2 |
| 2010/0220229 | A1 * | 9/2010 | Sano | G02B 13/0045 348/340 |
| 2010/0321564 | A1 * | 12/2010 | Feldman | G02B 9/12 348/374 |
| 2011/0032409 | A1 * | 2/2011 | Rossi | G02B 5/005 348/340 |
| 2012/0075519 | A1 * | 3/2012 | Blasch | G02B 7/102 348/340 |
| 2012/0257292 | A1 | 10/2012 | Lu | |
| 2013/0229719 | A1 | 9/2013 | Ovrutsky et al. | |
| 2014/0326855 | A1 | 11/2014 | Lu et al. | |
| 2014/0347748 | A1 | 11/2014 | Duparre | |
| 2017/0070687 | A1 * | 3/2017 | Endsley | H04N 5/2256 |

* cited by examiner

*Primary Examiner* — Abdelaaziz Tissire

(57) ABSTRACT

A camera module comprises an image sensor and a lens module disposed on the image sensor. The lens module comprises a top glass structure at top of the lens module. The top glass structure includes a first glass substrate, a second glass substrate, and a baffle disposed immediately between the first and the second glass substrates. The top glass structure is an outermost layer of the camera module. The lens module also comprises a bottom glass substrate at bottom of the lens module. The bottom glass substrate is disposed on the image sensor.

20 Claims, 4 Drawing Sheets

CAMERA MODULE HAVING BAFFLE BETWEEN TWO GLASS SUBSTRATES

FIELD OF THE INVENTION

This invention relates to a camera module, and more specifically relates to a camera module having baffle between two glass substrates.

BACKGROUND OF THE INVENTION

Camera modules are increasing in resolution but decreasing in size. Many small size camera modules on the order of 1 mm are available. Some of them are used in medical applications including endoscopy, which inserts camera modules into human body. When camera modules are inserted into human body, no toxic materials from the camera modules are allowed to expose to human body.

In a conventional camera module, a baffle, which blocks scattered light and flare in the camera module, is often placed on the outermost layer of the camera module. The baffle may be toxic to human body and may introduce health threats. For endoscopic applications, the baffle must be placed inside the camera module and does not expose to human body.

Furthermore, for many medical applications, the camera modules must be hermetically sealed and water resistant. Accordingly, hermetically sealed and water resistant camera modules that would not release toxic materials from inside the camera module, are demanded.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

Figure 1:
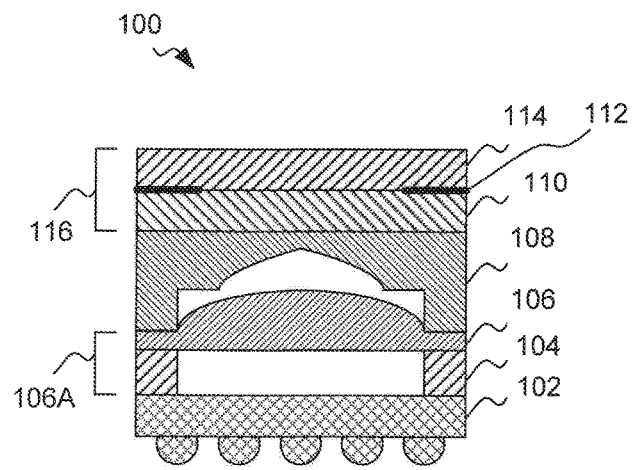
FIG. 1 illustrates an exemplary camera module having baffle between two glass substrates, in accordance with an embodiment of the present invention.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention.

DETAILED DESCRIPTION

In the following description, numerous specific details are set forth in order to provide a thorough understanding of the present invention. It will be apparent, however, to one having ordinary skill in the art that the specific detail need not be employed to practice the present invention. In other instances, well-known materials or methods have not been described in detail in order to avoid obscuring the present invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable combinations and/or sub-combinations in one or more embodiments.

FIG. 1 illustrates an exemplary camera module 100 in accordance with an embodiment of the present invention. Camera module 100 comprises an image sensor 102. A spacer 104 may be disposed on image sensor 102. A first lens 106, which is a replicated lens without micro structure, may be disposed on spacer 104. A second lens 108, which is a replicated lens with spacer, is disposed on first lens 106. Spacer 104 may be integrated with first lens 106, which is a replicated lens without micro structure, forming a replicated lens with spacer 106A similar to second lens 108. A first glass substrate 110 is disposed on second lens 108. A baffle 112 is disposed immediately on first glass substrate 110. Baffle 112 may be made of metal or other light blocking materials coated on first glass substrate 110. Baffle 112 may be a separate plate. The function of baffle 112 is to block unwanted light to enter camera module 100. Finally, a second glass substrate 114 is disposed immediately on baffle 112, so that baffle 112 is immediately between first glass substrate 110 and second glass substrate 114.

Second lens 108 may have a flat surface facing first glass substrate 110. The flat surface of second lens 108 may be in contact with first glass substrate 110. The flat surface of second lens 108 may be glued to first glass substrate 110.

First glass substrate 110, baffle 112, and second glass substrate 114 form a top glass structure 116. In an embodiment, the total thickness of top glass structure 116 is the same as the thickness of a single glass substrate used in a camera module. Top glass structure 116 is the top outermost layer of camera module 100.

A replicated lens is a wafer level lens. Multiple wafer level lenses are replicated using a mold on a substrate or wafer. In an embodiment, the substrate is removed from the replicated lenses. In another embodiment, the substrate stays with the replicated lenses. The substrate is transparent if it stays with the replicated lenses.

If baffle 112 is disposed on second lens 108, and is immediately between first glass substrate 110 and second lens 108, the present of baffle 112 will weaken the adhesion between first glass substrate 110 and second lens 108.

If baffle 112 is disposed on second glass substrate 114, baffle 112 is exposed to the outside of camera module 100. When camera module 100 is inserted inside human body, for example for endoscopic applications, the material of baffle 112 may be toxic to human body and introduce health threats.

Figure 2A:
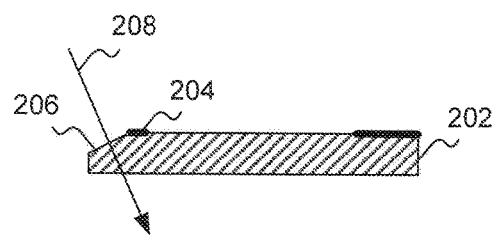
FIG. 2A illustrates a baffle disposed on a glass substrate.

FIG. 2A illustrate an exemplary singulated glass substrate 202 having a baffle 204 disposed on its surface exposed to the outside of a camera module. Glass substrate 202 may be a top outermost layer of a camera module. The singulated glass substrate 202 may have a chip 206 at a corner. Light 208 may penetrate through chip 206 to enter the camera module. Light penetrating and entering camera module is not desired and should be avoided.

Figure 2B:
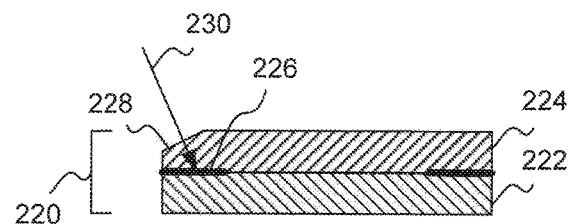
FIG. 2B illustrates a baffle disposed between two glass substrates, in accordance with an embodiment of the present invention.

FIG. 2B illustrates an exemplary singulated top glass structure 220 comprising a first glass substrate 222 and a second glass substrate 224, in accordance with an embodiment of the present invention. Top glass structure 220 may be a top outermost layer of a camera module. A baffle 226 is disposed between first glass substrate 222 and second glass substrate 224. Singulated top glass structure 220 may have a chip 228 at a corner. However baffle 226 is still intact and is not broken because of chip 228. Light 230 penetrating through chip 228 will be blocked by baffle 226 and cannot enter the camera module.

Figure 3:
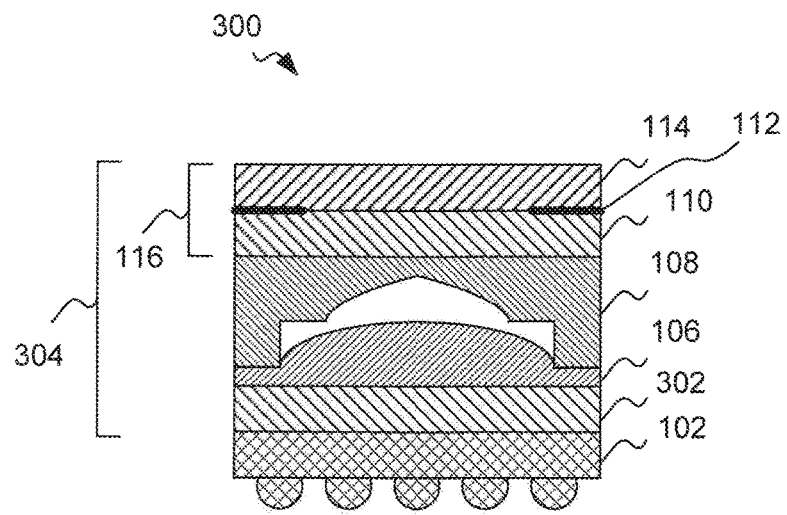
FIG. 3 illustrates an exemplary camera module of FIG. 1 further comprising a bottom glass substrate, in accordance with an embodiment of the present invention.

FIG. 3 illustrates an exemplary camera module 300 in accordance with an embodiment of the present invention. Camera module 300 is similar to camera module 100 of FIG. 1, except a bottom glass substrate 302 replaces spacer 104 of FIG. 1. Accordingly, a lens module 304 on top of image sensor 102 has bottom glass substrate 302 at the bottom and top glass structure 116 at the top. Top glass structure 116 is the top outermost layer of lens module 304, and bottom glass substrate 302 is the bottom outermost layer of lens module 304. Top glass structure 116 is also the top outermost layer of camera module 300. Bottom glass substrate 302 is disposed on image sensor 102. Bottom glass substrate 302 will shorten the camera module, as explained in the following.

Figure 4A:
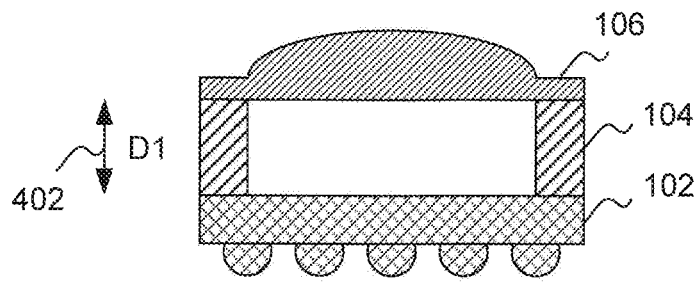
FIG. 4A illustrates a spacer disposed between an image sensor and a lens, in accordance with an embodiment of the present invention.

FIG. 4A illustrates spacer 104 disposed on image sensor 102, and first lens 106 disposed on spacer 104 (also shown in FIG. 1), in accordance with an embodiment of the present invention. A thickness 402 of spacer 104 is D1. The optical path length from first lens 106 to image sensor 102 is D1, since air having unity refractive index is in between first lens 106 and image sensor 102.

Figure 4B:
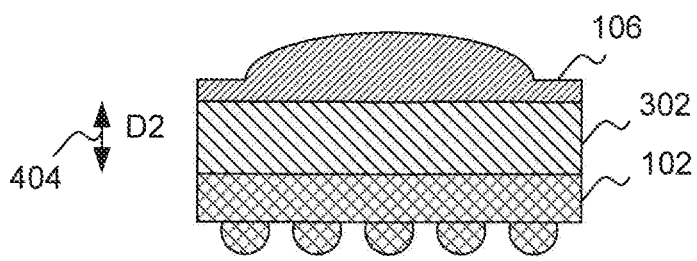
FIG. 4B illustrates a glass substrate disposed between an image sensor and a lens, in accordance with an embodiment of the present invention.

FIG. 4B illustrate bottom glass substrate 302 disposed on image sensor 102, and first lens 106 disposed on bottom glass substrate 302 (also shown in FIG. 3), in accordance with an embodiment of the present invention. A thickness 404 of bottom glass substrate 302 is D2. The optical path length from first lens 106 to image sensor 102 is the product of D2 and the refractive index (RI) of bottom glass substrate 302, since bottom glass substrate 302 is in between first lens 106 and image sensor 102. If the camera modules associated with FIG. 4A and FIG. 4B have the same optical system, the optical path lengths in FIG. 4A and FIG. 4B are the same. Accordingly, D1=D2×RI, where RI is refractive index of bottom glass substrate 302. Since RI is larger than unity, D2 is less than D1. Thus, bottom glass substrate 302 shortens the camera module.

Figure 5:
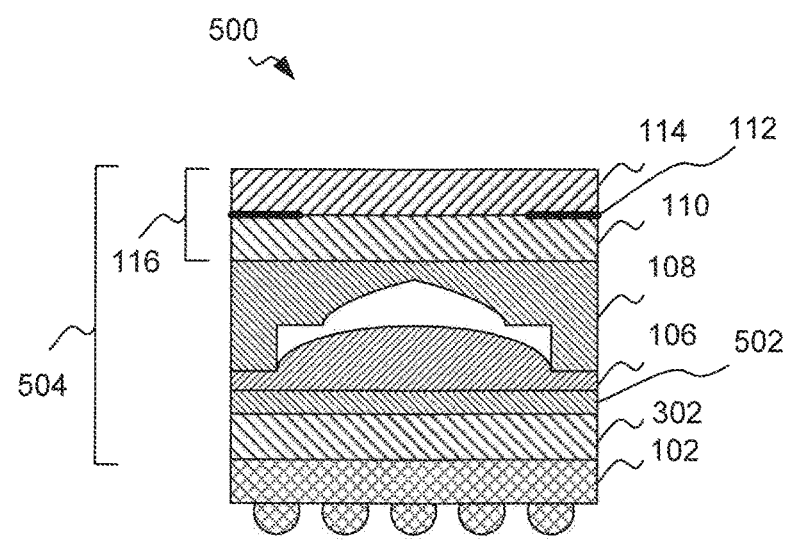
FIG. 5 illustrates an exemplary camera module of FIG. 3 further comprising an IR cut filter, in accordance with an embodiment of the present invention.

FIG. 5 illustrates an exemplary camera module 500 in accordance with an embodiment of the present invention. Camera module 500 is similar to camera module 300 of FIG. 3, except camera module 500 further comprises an IR cut filter 502. In another embodiment, camera module 500 may further comprise an IR pass filter (not shown) instead of IR cut filter 502. Accordingly, a lens module 504 on top of image sensor 102 has bottom glass substrate 302 at the bottom and top glass structure 116 at the top. Top glass structure 116 is the top outermost layer of lens module 504, and bottom glass substrate 302 is the bottom outermost layer of lens module 504. Top glass structure 116 is also the top outermost layer of camera module 500. It is appreciated that camera module 100 of FIG. 1 may also comprise an IR cur filter or an IR pass filter.

Figure 6:
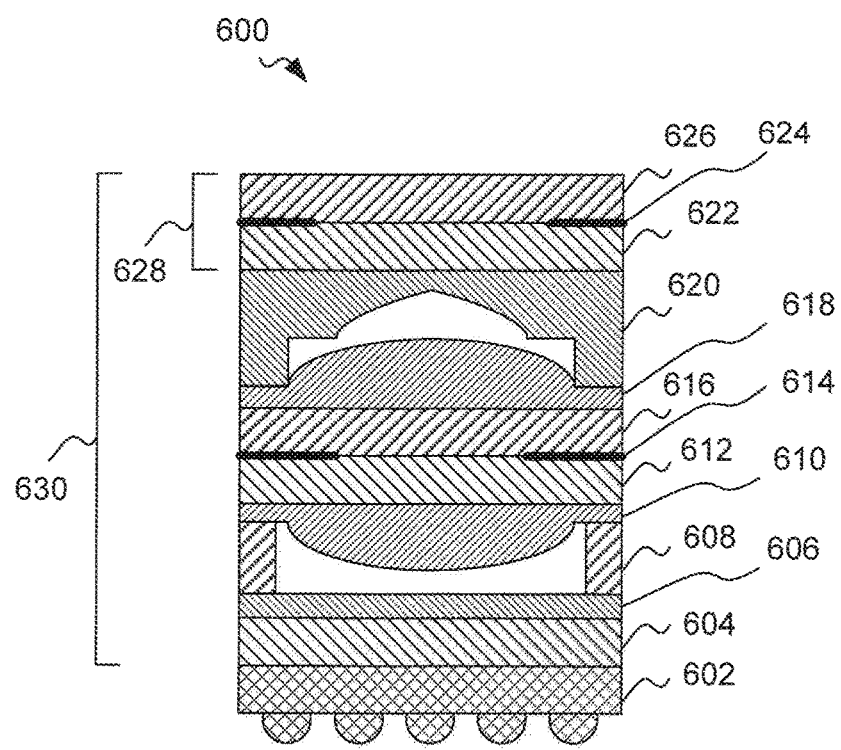
FIG. 6 illustrates an exemplary camera module of FIG. 5 comprising multiple lenses, in accordance with an embodiment of the present invention.

FIG. 6 illustrates an exemplary camera module 600 in accordance with an embodiment of the present invention. Camera module 600 comprises an image sensor 602. A bottom glass substrate 604 is disposed on image sensor 602. An IR cut filter 606 may be disposed on bottom glass substrate 604. A spacer 608 may be disposed on IR cut filter 606. A first lens 610, which may be a replicated lens without micro structure, may be disposed on spacer 608. A first glass substrate 612 may be disposed on first lens 610. A stop aperture 614 may be disposed on first glass substrate 612. A second glass substrate 616 may be disposed on stop aperture 614. Stop aperture 614 is between first glass substrate 612 and second glass substrate 616.

A second lens 618, which may be a replicated lens without micro structure, may be disposed on second glass substrate 616. A third lens 620, which is a replicated lens with spacer, may be disposed on second lens 618. A third glass substrate 622 is disposed on third lens 620. A baffle 624 is disposed immediately on third glass substrate 622. Baffle 624 may be made of metal or other light blocking materials coated on third glass substrate 622. Baffle 624 may be a separate plate. The function of baffle 624 is to block unwanted light to enter camera module 600. Finally, a fourth glass substrate 626 is disposed immediately on baffle 624, so that baffle 624 is immediately between third glass substrate 622 and fourth glass substrate 626. Third glass substrate 622, baffle 624, and fourth glass substrate 626 form a top glass structure 628.

Third lens 620 may have a flat surface facing third glass substrate 622. The flat surface of third lens 620 may be in contact with third glass substrate 622. The flat surface of third lens 620 may be glued to third glass substrate 622.

In this manner, a lens module 630 having bottom glass substrate 604 at the bottom and top glass structure 628 at the top is formed. Top glass structure 628 is the top outermost layer of lens module 630, and bottom glass substrate 604 is the bottom outermost layer of lens module 630. Lens module 630 may be disposed on image sensor 602 to form camera module 600. Top glass structure 628 is also the top outermost layer of camera module 600.

In the wafer level manufacturing practice, all layers including replicated lenses, spacers, and glass substrates, are bonded using UV glue or thermal glue. Accordingly, the structure of lens module 630 becomes hermetically sealed and water resistant. The elements in lens module 630 that may include replicated lenses, baffle, and stop, are enclosed by bottom glass substrate 604 at the bottom, top glass structure 628 at the top, and bonding glue on the side of the lens module. Thus, even if the materials of the elements are toxic to human body, they cannot be exposed to human body. In an embodiment, a flat bottom glass substrate makes it easier to bond the lens module with an image sensor including CSP (chip scale packaging) sensor. In an embodiment, with suitable packaging process, camera module 600 is also hermetically sealed and water resistant.

Lens module 630 and camera module 600 may be installed in an endoscope and/or other medical apparatus. Lens module 630 and camera module 600 are hermetically sealed and water resistant.

It is appreciated that first lens 610, second lens 618, and third lens 620 are not limited to wafer level lenses, other types of lenses including casting and molded lenses are also usable.

It is appreciated that a lens module having a bottom glass substrate at the bottom and a top glass structure at the top may comprise only one lens, two lenses, three lenses, and more than three lenses.

Figure 7:
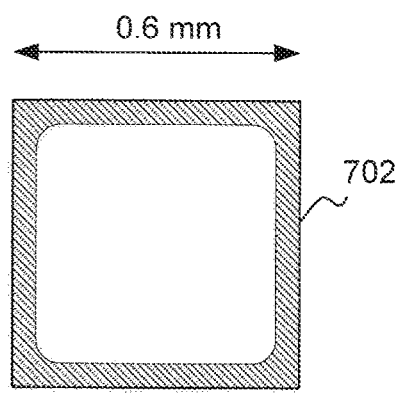
FIG. 7 illustrates an exemplary cross section of a baffle, in accordance with an embodiment of the present invention.

FIG. 7 illustrates an exemplary cross section of a baffle 702 in accordance with an embodiment of the present invention. The cross section may be square, rectangular, circular, elliptical, or any shape. The baffle is around the edge of the cross section, and no baffle in the center. For example, a side of cross section of baffle 702 is 0.6 mm.

While the present invention has been described herein with respect to the exemplary embodiments and the best mode for practicing the invention, it will be apparent to one of ordinary skill in the art that many modifications, improvements and sub-combinations of the various embodiments, adaptations and variations can be made to the invention without departing from the spirit and scope thereof.

The terms used in the following claims should not be construed to limit the invention to the specific embodiments disclosed in the specification and the claims. Rather, the scope is to be determined entirely by the following claims, which are to be construed in accordance with established doctrines of claim interpretation. The present specification and figures are accordingly to be regarded as illustrative rather than restrictive.

What is claimed is:

1. A camera module comprising:
   an image sensor; and
   a lens module disposed on the image sensor, the lens module comprising:
   a top glass structure at top of the lens module, the top glass structure consisting of a first glass substrate, a second glass substrate, and a baffle disposed immediately between the first and the second glass substrates;
   wherein the top glass structure is an outermost layer of the camera module.

2. The camera module of claim 1, the lens module further comprising:
   a bottom glass substrate at bottom of the lens module, wherein the bottom glass substrate is disposed on the image sensor.

3. The camera module of claim 1, the lens module further comprising at least a lens.

4. The camera module of claim 3, wherein the lens has a flat surface and wherein the flat surface is glued to one of the first glass substrate and the second glass substrate.

5. The camera module of claim 3, wherein the lens is a wafer level lens.

6. The camera module of claim 3, wherein the lens is a casting lens.

7. The camera module of claim 3, wherein the lens is a molded lens.

8. The camera module of claim 1, the lens module further comprising an IR cut filter.

9. The camera module of claim 1, the lens module further comprising an IR pass filter.

10. The camera module of claim 1, the lens module further comprising a stop aperture disposed between two glass substrates.

11. The camera module of claim 1, the lens module further comprising a spacer.

12. The camera module of claim 1, wherein layers in the lens module are bonded using one of UV glue and thermal glue.

13. The camera module of claim 1, wherein the camera module is hermetically sealed.

14. The camera module of claim 1, wherein the camera module is water resistant.

15. The camera module of claim 1, wherein the camera module is installed in an endoscope.

16. A lens module comprising:
   a top glass structure at top of the lens module, the top glass structure consisting of a first glass substrate, a second glass substrate, and a baffle disposed immediately between the first and the second glass substrates;
   a bottom glass substrate at bottom of the lens module;
   at least a lens disposed between the top glass structure and the bottom glass substrate;
   wherein the top glass structure is an outermost layer of the lens module.

17. The lens module of claim 16, wherein layers in the lens module are bonded using one of UV glue and thermal glue.

18. The lens module of claim 16, wherein the lens module is hermetically sealed.

19. The lens module of claim 16, wherein the lens module is water resistant.

20. The lens module of claim 16, wherein the lens module is installed in an endoscope.

* * * * *